United States Patent
Ko

(10) Patent No.: US 11,793,791 B1
(45) Date of Patent: Oct. 24, 2023

(54) SOLUBILIZATION METHOD OF BENZIMIDAZOLE-BASED COMPOUND AND USE THEREOF

(71) Applicant: SUN & PINE TREE Co., Ltd, Jeollabuk-do (KR)

(72) Inventor: Jang Ho Ko, Jeollabuk-do (KR)

(73) Assignee: SUN & PINE TREE Co., Ltd, Jeollabuk-Do (KR)

( * ) Notice: Subject to any disclaimer, the term of this patent is extended or adjusted under 35 U.S.C. 154(b) by 0 days.

(21) Appl. No.: 18/093,385

(22) Filed: Jan. 5, 2023

(51) Int. Cl.
*A61K 31/4184* (2006.01)
*A61P 3/10* (2006.01)
*A61K 9/107* (2006.01)
*A61K 47/44* (2017.01)

(52) U.S. Cl.
CPC .......... *A61K 31/4184* (2013.01); *A61K 9/107* (2013.01); *A61K 47/44* (2013.01); *A61P 3/10* (2018.01)

(58) Field of Classification Search
CPC .............................. A61K 31/4184; A61P 3/10
See application file for complete search history.

(56) References Cited

FOREIGN PATENT DOCUMENTS

| KR | 10-1247803 | B1 | 4/2013 |
| KR | 10-2022-0065475 | A | 5/2022 |

*Primary Examiner* — Kamal A Saeed
(74) *Attorney, Agent, or Firm* — The PL Law Group, PLLC

(57) ABSTRACT

A method for solubilizing a benzimidazole-based compound according to an embodiment includes preparing a first mixture solution by adding a benzimidazole-based compound to a solution in which water and glycerin are mixed with each other and subsequently homogenizing the first mixture, admixing the first mixture solution with plant oil and an emulsifier in order to prepare a second mixture and subsequently homogenizing the second mixture, and after the admixing, allowing the second mixture to stand at 0 to 10° C. for 12 to 48 hours to obtain a solubilized product of the benzimidazole-based compound. The solubilization method is advantageous in that, as the processing is carried out by using a material having no human toxicity, the step of removing solvents that are harmful to human can be omitted, and a solubilized product with human safety and high effect can be provided.

10 Claims, 9 Drawing Sheets

SOLUBILIZATION METHOD OF BENZIMIDAZOLE-BASED COMPOUND AND USE THEREOF

BACKGROUND

1. Technical Field

The present invention relates to a solubilization method of benzimidazole-based compound and use thereof.

2. Background Art

Sparingly soluble drugs are a drug compound that is hardly soluble in water as it contains a hydrophobic moiety in the structure. Due to the poor solubility, they often have limited practical use. For example, at least 41% or so of the drugs developed as a new pharmaceutical drug are abandoned during the developmental process due to the poor solubility and a least one third or so of the drugs that are described in US Pharmacopeia are classified as sparingly soluble drug.

To actually use those sparingly soluble drugs, it is necessary to add additional materials for solving the poor solubility problem. However, many studies indicating limited use due to toxicity of the additional materials are reported. For example, to solubilize a sparingly soluble material, emulsification using emulsifier, entrapping using liposome, or the like are widely carried out. However, due to the incorporation of foreign materials not originating from human body, physical instability, or the like, those conventional methods are used only in a limited way.

Accordingly, more efforts are needed to achieve, while not containing an excessive amount of emulsifier, stabilizer, and vehicle, the long-term stability by preventing the deterioration caused by conditions like temperature, storage area, and storage period and maintain homogeneous aqueous solution state of pharmaceutical products that are made of sparingly soluble materials.

Meanwhile, benzimidazole is a chemical compound having an imidazole ring attached to a benzene ring. By having various activities and physiological functions, it draws attention as a mother nucleus of many drug compounds. It has been reported that, depending on various substituent groups, compounds with such benzimidazole structure are effective for many different disorders. For example, compounds have been developed as an anti-inflammatory pain reliever, an anti-microbial agent, an anti-parasitic agent, an anti-histamine agent, and the like.

However, albendazole, mebendazole, and flubendazole, which are the representative examples of a benzimidazole-based compound, are all sparingly soluble drugs and disadvantageous in that, upon oral administration, they exhibit significantly low bioavailability. Accordingly, efforts are needed to achieve the solubilization of albendazole, mebendazole, and flubendazole as sparingly soluble drug.

Meanwhile, diabetes is one kind of metabolic disorders showing insufficient secretion amount or abnormal activity of insulin, and it is characterized by high blood sugar level indicating high concentration of glucose in blood. As a result of the high blood sugar level, many symptoms and signs are exhibited and glucose is discharged in urine.

Diabetes is classified into Type 1 diabetes and Type 2 diabetes, in which Type 1 diabetes is a disorder as no insulin is produced at all and Type 2 diabetes is characterized by the insulin resistance, in which, due to relative deficiency of insulin, the activity of insulin for reducing blood sugar level is impaired so that glucose is not effectively oxidized in cells.

Type 2 diabetes accounts for around 90% of all diabetes cases. Due to the prevalence of obesity in population caused by a shift to lifestyle with low physical activity and westernized diet, Type 2 diabetes tends to increase dramatically in recent years. The most effective therapy for Type 2 diabetes is to have the optimum blood sugar level after eating.

Meanwhile, in Korea Patent Registration No. 2455423, a solubilized composition with improved water solubility by forming micelle by enclosing fenbendazole in a specific macromolecular polymer and a use of the fenbendazole-solubilized composition as a material of medicinal product are described. In addition, in Korea Patent Registration No. 1247803, an aqueous solubilization solution composition, which takes an advantage of cancellation of the interaction between molecules of a hydrophobic material by mannosylerythritol lipids without having any physical requirement, and a method for solubilizing an aqueous solution of a sparingly soluble material are described. However, the solubilization method of benzimidazole-based compound of the present invention, which comprises preparing a first mixture solution by adding a benzimidazole-based compound to a solution in which water and glycerin are mixed with each other and subsequently homogenizing them at high speed, admixing the first mixture solution with plant oil and an emulsifier in order and subsequently homogenizing them at high speed, and allowing the mixture to stand at 0 to 10° C. for 12 to 48 hours, is not disclosed before.

SUMMARY

The present invention is devised under the circumstances that are described in the above, and provided in the present invention is a solubilization method of benzimidazole-based compound comprising preparing a first mixture solution by adding a benzimidazole-based compound to a solution in which water and glycerin are mixed with each other and subsequently homogenizing them at high speed, admixing the first mixture solution with plant oil and an emulsifier in order and subsequently homogenizing them at high speed, and allowing the mixture to stand at 0 to 10° C. for 12 to 48 hours. By finding that the anti-diabetic effect of a solubilized product of the benzimidazole-based compound processed by the aforementioned solubilization method is higher than the effect of conventional benzimidazole-based compounds, the present invention is completed accordingly.

To solve the problem described above, the present invention provides a solubilization method of benzimidazole-based compound comprising:

1) preparing a first mixture solution by adding a benzimidazole-based compound to a solution in which water and glycerin are mixed with each other and subsequently homogenizing them at high speed;
2) admixing the first mixture solution of the step 1) with plant oil and an emulsifier in order and subsequently homogenizing them at high speed, and 3) after the step 2), allowing the mixture to stand at 0 to 10° C. for 12 to 48 hours.

The present invention further provides a solubilized product of benzimidazole-based compound processed by the aforementioned solubilization method.

The present invention further provides a pharmaceutical composition for preventing or treating diabetes comprising the solubilized product of benzimidazole-based compound as an effective component.

The present invention still further provides a veterinary composition for preventing or treating diabetes comprising the solubilized product of benzimidazole-based compound as an effective component.

The present invention relates to a solubilization method of benzimidazole-based compound and use thereof. Specifically, the solubilized product of benzimidazole-based compound, which has been processed by the solubilization method comprising preparing a first mixture solution by adding a benzimidazole-based compound to a solution in which water and glycerin are mixed with each other and subsequently homogenizing them at high speed, admixing the first mixture solution with plant oil and an emulsifier in order and subsequently homogenizing them at high speed, and allowing the mixture to stand at 0 to 10° C. for 12 to 48 hours, showed a remarkably improved anti-diabetic effect compared to conventional benzimidazole-based compounds.

Furthermore, the solubilization method of the present invention is advantageous in that, as the processing is carried out by using a material having no human toxicity, the step of removing solvents that are harmful to human is not required, and a solubilized product with human safety and high effect can be provided.

BRIEF DESCRIPTION OF THE DRAWINGS

Specifically, Control represents the group not treated with any test material, Test example 1 represents the group administered with the solubilized product of mebendazole which has been processed by the solubilization method of the present invention, Comparative example 1 represents the group administered with conventional mebendazole mixed with water, and Comparative example 2 represents the group administered with conventional mebendazole mixed with corn oil. Empagliflozin, Sitagliptin, and Metformin correspond to a positive control in which empagliflozin, sitagliptin, or metformin has been administered as an oral therapeutic agent for treating diabetes. In FIG. 2B, the different letters a to d indicate that there is a statistically significant difference, i.e., $p<0.05$.

Specifically, Control represents the group not treated with any test material, Test example 1 represents the group administered with the solubilized product of mebendazole which has been processed by the solubilization method of the present invention, Comparative example 1 represents the group administered with conventional mebendazole mixed with water, and Comparative example 2 represents the group administered with conventional mebendazole mixed with corn oil. Empagliflozin, Sitagliptin, and Metformin correspond to a positive control to which empagliflozin, sitagliptin, or metformin has been administered as an oral therapeutic agent for treating diabetes.

In FIG. 4, the different letters a and b indicate that there is a statistically significant difference, i.e., $p<0.05$.

In FIG. 5, the different letters a and b indicate that there is a statistically significant difference, i.e., $p<0.05$.

In FIG. 6, the different letters a to d indicate that there is a statistically significant difference, i.e., $p<0.05$.

In FIG. 7, the different letters a to f indicate that there is a statistically significant difference, i.e., $p<0.05$.

DETAILED DESCRIPTION

Figure 1:
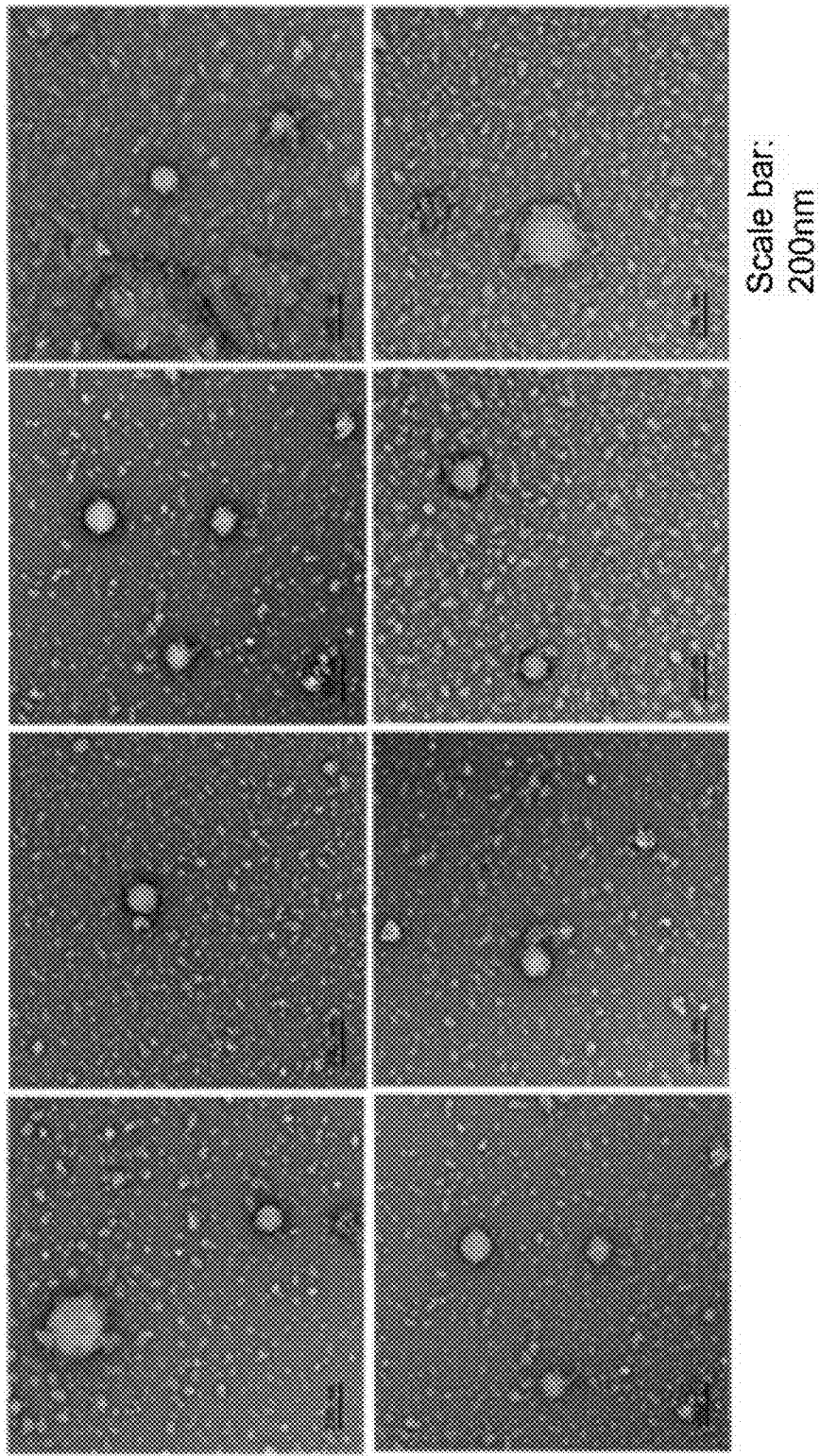
FIG. 1 is a TEM (transmission electron microscopy) photographic image of the processed product of mebendazole, which has been processed by the solubilization method of the present invention. After mixing 3.75 mg of the processed product of mebendazole with 1 mL of water, a TEM photographic image was taken.

To solve the problem described above, the present invention provides a solubilization method of benzimidazole-based compound comprising:
1) preparing a first mixture solution by adding a benzimidazole-based compound to a solution in which water and glycerin are mixed with each other and subsequently homogenizing them at high speed;
2) admixing the first mixture solution of the step 1) with plant oil and an emulsifier in order and subsequently homogenizing them at high speed, and
3) after the step 2), allowing the mixture to stand at 0 to 10° C. for 12 to 48 hours.

The benzimidazole-based compound is preferably any one selected from mebendazole and flubendazole. It is more preferably mebendazole, but not limited thereto.

As for the plant oil, it is possible to use any type of plant oil. Examples thereof include olive oil, sesame oil, rice bran oil, soybean oil, canola oil, corn oil, palm oil, sunflower oil, cottonseed oil, coconut oil, and grapeseed oil. Preferably, it is canola oil, but it is not limited thereto.

As for the emulsifier, any type of emulsifier can be used as long as it is made of edible components. It is preferable to use a non-ionic surfactant. It is more preferable to use sucrose fatty acid ester, but it is not limited thereto.

The solubilization method of benzimidazole-based compound preferably includes:
1) preparing a first mixture solution by adding mebendazole or flubendazole to a solution in which water and glycerin are mixed with each other and subsequently homogenizing them at high speed of 3,000 to 5,000 rpm and temperature of 50 to 80° C.;
2) admixing the first mixture solution of the step 1) with canola oil and sucrose fatty acid ester in order and subsequently homogenizing them at high speed of 10,000 to 30,000 rpm and temperature of 50 to 70° C., and
3) after the step 2), allowing the mixture to stand at 2 to 6° C. for 20 to 30 hours.

The solubilization method of benzimidazole-based compound more preferably includes:
1) preparing a first mixture solution by adding 3 to 7 g of mebendazole or flubendazole to a solution in which 100 g of water and 30 to 50 g of glycerin are mixed with each other and subsequently homogenizing them at high speed of 3,500 to 4,500 rpm and temperature of 65 to 75° C.;
2) admixing the first mixture solution of the step 1) with 8 to 12 g of canola oil and 10 to 20 g of sucrose fatty acid ester in order and subsequently homogenizing them at high speed of 15,000 to 25,000 rpm and temperature of 55 to 65° C., and
3) after the step 2), allowing the mixture to stand at 3 to 5° C. for 20 to 28 hours.

The solubilization method of benzimidazole-based compound even more preferably includes:
1) preparing a first mixture solution by adding 5 g of mebendazole or flubendazole to a solution in which 100 g of water and 40 g of glycerin are mixed with each other and subsequently homogenizing them at high speed of 4,000 rpm and temperature of 70° C.;
2) admixing the first mixture solution of the step 1) with 10 g of canola oil and 15 g of sucrose fatty acid ester in order and subsequently homogenizing them at high speed of 20,000 rpm and temperature of 60° C., and
3) after the step 2), allowing the mixture to stand at 4° C. for 24 hours, but it is not limited thereto.

According to one embodiment of the present invention, the solubilized product of benzimidazole-based compound including mebendazole, flubendazole, and albendazole which has been processed by the aforementioned solubilization method is effective for enhancing the anti-diabetic effect when compared to mebendazole, flubendazole, and albendazole that are conventionally used.

The present invention further provides a solubilized product of benzimidazole-based compound processed by the aforementioned solubilization method.

The benzimidazole-based compound is preferably mebendazole or flubendazole, but it is not limited thereto.

The present invention further provides a pharmaceutical composition for preventing or treating diabetes including the solubilized product of benzimidazole-based compound as an effective component.

According to one embodiment of the present invention, the solubilized product of benzimidazole-based compound has an excellent effect of enhancing the glucose tolerance.

Other than the effective component described above, the composition of the present invention may further include a pharmaceutically acceptable carrier, vehicle, or diluent. The composition of the present invention can be in various types of formulation such as oral formulation or parenteral formulation.

The pharmaceutical composition according to the present invention is administered in a pharmaceutically effective amount. As described herein, the expression "pharmaceutically effective amount" means an amount sufficient for treating a disorder at reasonable benefit-risk ratio that can be applied for a medical treatment. The effective dose level may be determined based on a type or severeness of a disorder of a patient, activity of a pharmaceutical, sensitivity to a pharmaceutical, administration period, administration route, excretion ratio, time period for therapy, elements including a pharmaceutical used in combination, and other elements that are well known in the medical field.

The present invention still further provides a veterinary composition for preventing or treating diabetes including the solubilized product of benzimidazole-based compound as an effective component.

The benzimidazole-based compound is preferably mebendazole or flubendazole, but it is not limited thereto.

The veterinary composition of the present invention may further include a vehicle and a diluent according to a common method. Examples of the vehicle and diluent which may be included in veterinary composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, non-crystalline cellulose, polyvinyl pyrrolidone, water, methylhydroxy benzoate, propylhydroxy benzoate, talc, magnesium stearate, cetanol, stearyl alcohol, fluid paraffin, sorbitan monostearate, polysorbate 60, methyl paraben, propyl paraben, and mineral oil. The veterinary composition of the present invention may additionally include a filler, an anti-aggregation agent, a lubricant, a wetting agent, a fragrance, an emulsifier, and a preservative.

The veterinary composition of the present invention may be formulated by using a method well known in the pertinent art such that the active component is released either rapidly, continuously, or extendedly after it is administered to an animal. Examples of the formulation type include a powder, a granule, a tablet, a capsule, a suspension, an emulsion, a solution, a syrup, an aerosol, a soft or hard gelatin capsule, a suppository, a sterile injection solution, and a sterile formulation for external application.

Hereinbelow, the present invention is explained in greater detail in view of the Examples. However, the following Examples are given only for more specific explanation of the present invention and it would be evident to a person who has common knowledge in the pertinent art that the scope of the present invention is not limited by them.

Examples

Materials and Methods
1. Solubilization of Benzimidazole-Based Compound

To a solution in which 100 g of water are mixed with 40 g of glycerin, 5 g of mebendazole were added followed by high speed homogenization at speed of 4,000 rpm and temperature of 70° C. to give a first mixture solution. After that, the first mixture solution was admixed with 10 g of canola oil and 15 g of sucrose fatty acid ester in order and subsequently subjected to homogenization at high speed of 20,000 rpm and temperature of 60° C. Then, after stabilizing the mixture by allowing it to stand at 4° C. for 24 hours, a solubilized product of mebendazole was obtained as milk white solution (Test example 1).

After admixing 3.75 mg of the solubilized product of mebendazole with 1 mL of water, a photographic image was taken by using a transmission electron microscope. As a result, it was found that liposomes are formed as illustrated in FIG. 1. Content of mebendazole within the liposome processed by the method described above was found to be 2.941% relative to the total weight.

Moreover, by carrying out the solubilization in the same manner as above while using flubendazole instead of mebendazole, a solubilized product of flubendazole was obtained (Test example 2).

Moreover, by carrying out the solubilization in the same manner as above while using albendazole instead of mebendazole, a solubilized product of albendazole was obtained (Test example 3).

Moreover, as a comparative example of the solubilized products described above, a mixture solution in which conventional mebendazole has been mixed with water (Comparative example 1), a mixture solution in which conventional mebendazole has been mixed with corn oil (Comparative example 2), a mixture solution in which conventional flubendazole has been mixed with water (Comparative example 3), and a mixture solution in which conventional albendazole has been mixed with water (Comparative example 4) were used.

2. Preparation of Test Material

Test material for determining the anti-diabetic effect was prepared as described in the following Table 1, and it was orally administered to a mouse.

TABLE 1

| Test Group | Test Material | Dilution Buffer | Dose (based on test material) |
| --- | --- | --- | --- |
| Test example 1 | Solubilized product of mebendazole | — | 5 mg/kg |
| Test example 2 | Solubilized product of flubendazole | — | 5 mg/kg |
| Test example 3 | Solubilized product of albendazole | — | 5 mg/kg |
| Comparative example 1 | Mebendazole | D.W | 5 mg/kg |
| Comparative example 2 | Mebendazole | Corn oil | 5 mg/kg |
| Comparative example 3 | Flubendazole | D.W | 5 mg/kg |
| Comparative example 4 | Albendazole | D.W | 5 mg/kg |
| Positive control | Empagliflozin | D.W | 10 mg/kg |
|  | Sitagliptin | D.W | 10 mg/kg |
|  | Metformin | D.W | 300 mg/kg |

3. Determination of Anti-Diabetic Effect
1) Test Animal and Breeding Condition

As for the test animal, a 6-week old male ICR mouse in SPF (specific-pathogen free) state was obtained from Samtako Korea (Kyuing-gi Province, South Korea). After the acclimation for 7 days, the animals were brought into use for the test. During the acclimation period, the animals were provided with general solid feeds (Purina Lab Rodent Chow #38057, Purina Co.) as test diet, and they were allowed to have free access to filtered drinking water which has been freshly provided every day. The test was carried out in accordance with the Ethics Regulation for Animal Testing of InVivo Corp. (Approval No.: IV-RA-06-2202-04-R).

2) Environmental Condition

Test animals were kept in a polycarbonate breeding box, 10 animals per each box. During the breeding period, the temperature and humidity were maintained at 22±2° C. and 50±10%, respectively. The environmental condition as follows was also maintained: illumination time and light/dark cycle of 12 hours per day (07:00 to 19:00), and air ventilation of 10 times per hour.

3) Test Group Setting and Test Sample Administration

Test animals after completion of the acclimation were separated by using random block design such that, in terms of fasting blood sugar, the mean value is even among different groups. By carrying out ear punch, identification of each animal was achieved. The test group includes Control group, Test example 1 administration group, Test example 2 administration group, Test example 3 administration group, Comparative example 1 administration group, Comparative example 2 administration group, Comparative example 3 administration group, Comparative example 4 administration group, empagliflozin administration group, sitagliptin administration group, and metformin administration group, and 10 animals per each group were brought into use for the test.

4) Oral Glucose Tolerance Test (OGTT) and Oral Sucrose Tolerance Test (OSTT)

Fasting sugar level was measured from the tail vein of a test animal which has been fasted for at least 8 hours. Then, the animal was orally administered with a test sample for each test group. The blood sugar level was measured again after 30 minutes, and then the animal was administered with glucose or sucrose, 2 g/kg for each. From the administration to 120 minutes after the administration, blood sugar level was measured with an interval of 30 minutes. Based on the measured blood sugar level, a change in blood sugar level was analyzed for each test group.

4. Statistical Analysis

With regard to the statistical analysis based on determination of statistical significance among different groups, comparison between ANOVA (one-way analysis of variance test) and Duncan post-hoc test was made. When the result is p<0.05, it was determined as significant (SPSS V12., SPSS Inc).

Example 1. Anti-Diabetic Effect of Solubilized Product of Benzimidazole-Based Compound 1) Mebendazole Fasting blood sugar level and postprandial blood sugar level are the indicator of blood sugar control. Hyperglycemia is deeply related with the risk of having a complication of great arteries and it has been reported to be the cause of having high mortality among patients suffering from diabetes. Glucose absorbed in human body is either oxidized in peripheral tissues or stimulates beta cells to secrete insulin, thus controlling sugar level in human body. This property of human body for normally metabolizing glucose is called 'glucose tolerance', and hyperglycemia may be caused by impaired glucose tolerance. Accordingly, to determine the blood sugar-controlling effect of test sample, a glucose tolerance test was carried out for an animal.

Figure 2A:
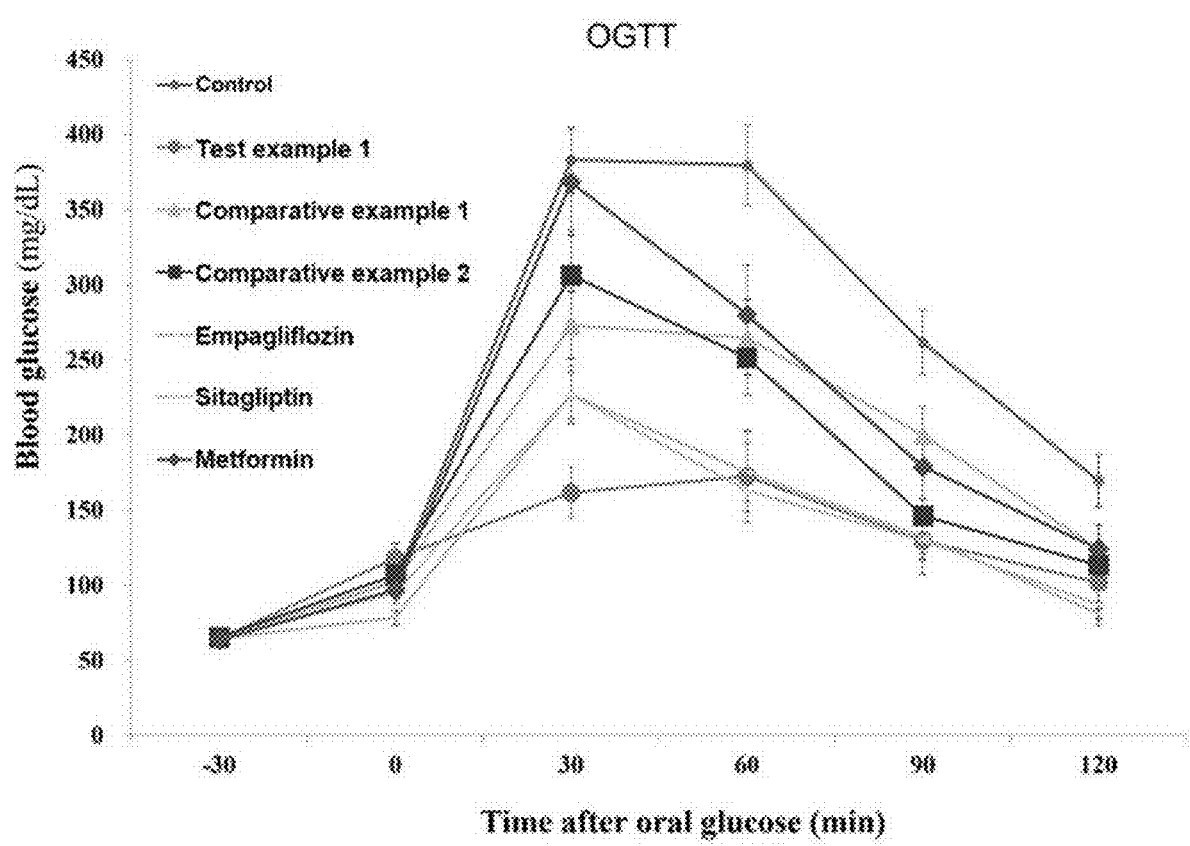
FIG. 2A is the result of OGTT (oral glucose tolerance test) of mebendazole.

As a result of the oral glucose tolerance test (OGTT), fasting glucose level (−30 min), which is before the administration of test sample, showed no significant difference in all test groups as it is illustrated in FIG. 2A. In terms of the blood sugar level after the administration of test sample (i.e., 0 min), there was no remarkable difference between Control and all test groups. However, 30 minutes after the administration of test sample, the test administration groups showed lower blood sugar level compared to Control. In particular, it was found that the solubilized product of mebendazole (Test example 1) can most effectively suppress an increase in blood sugar level.

Figure 2B:
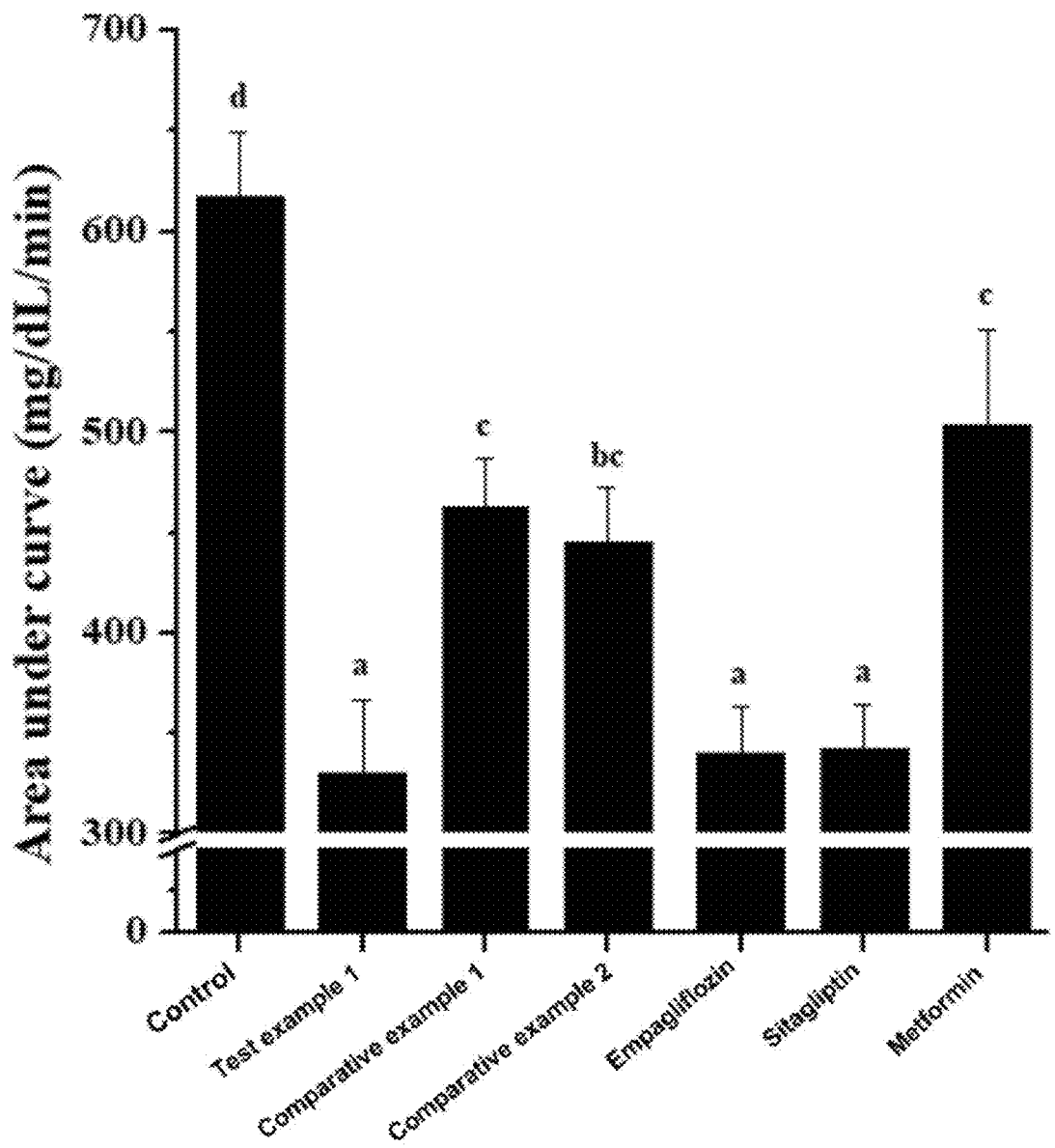
FIG. 2B the result of analyzing the area under curve of graph in FIG. 2A.

Furthermore, as a result of analyzing the area under curve of the oral glucose tolerance test, it was found that the test sample administration groups have more excellent effect of suppressing an increase in blood sugar level compared to Control as it is shown in FIG. 2B. In addition, compared to the group administered with conventional mebendazole mixed with water (Comparative example 1) and the group administered with conventional mebendazole mixed with corn oil (Comparative example 2), the group administered with the solubilized product of mebendazole (Test example 1), which has been processed by the solubilization method of the present invention, showed a significantly reduced area under curve, indicating that it has an excellent effect of suppressing an increase in blood sugar level.

Meanwhile, sucrose as a polymerization product between glucose and fructose is degraded by α-glucosidase to yield glucose and fructose, which are absorbed into blood vessels of small intestine, yielding an increase in blood sugar level. Accordingly, the anti-diabetic effect of test sample was determined by oral sucrose tolerance test (OSTT).

Figure 3A:
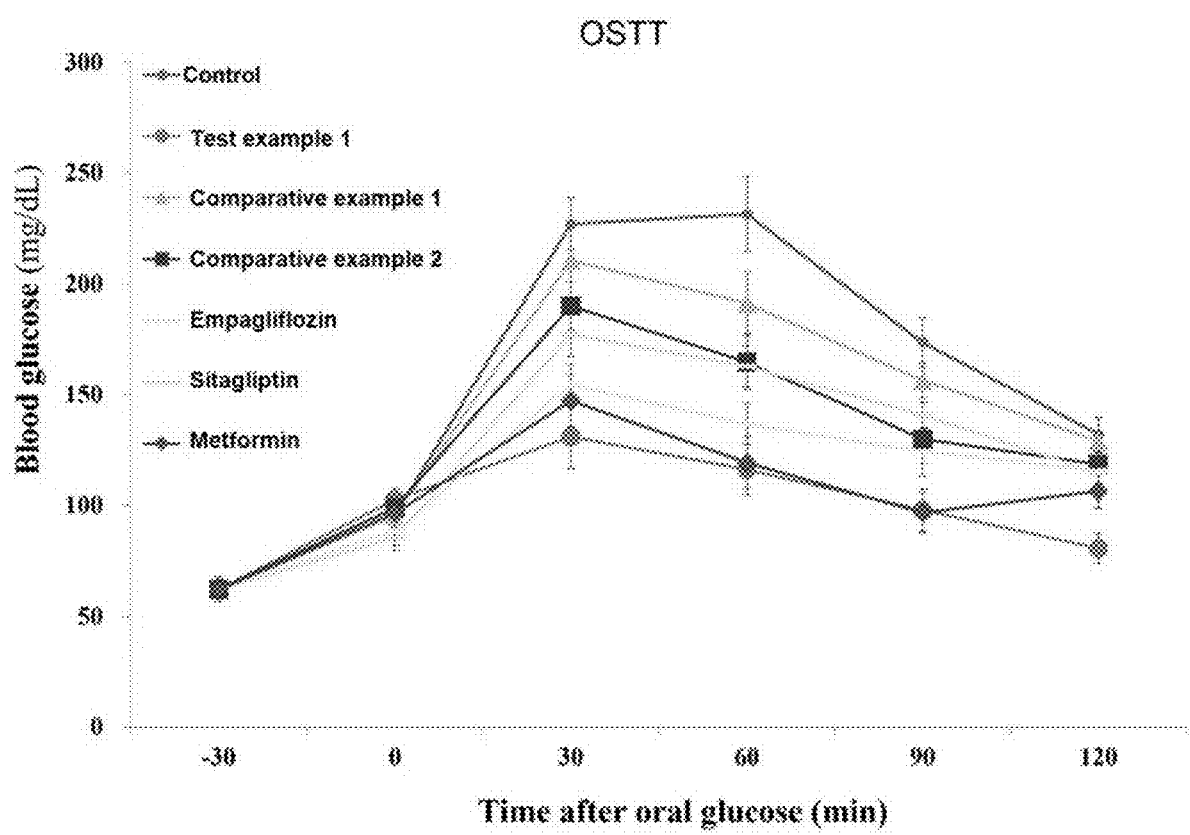
FIG. 3A is the result of OSTT (oral sucrose tolerance test) of mebendazole and FIG. 3B the result of analyzing the area under curve of graph in FIG. 3A.

As a result of the oral sucrose tolerance test (OSTT), compared to Control, both the fasting glucose level and blood sugar level right after administering each test sample (i.e., 0 min) showed no significant difference in all test groups as it is illustrated in FIG. 3A. However, 30 minutes after the administration of test sample, the group administered with solubilized product of mebendazole processed by the solubilization method of the present invention (Test example 1) showed a remarkably reduced increase in blood sugar level compared to the group administered with conventional mebendazole mixed with water (Comparative example 1) and also the group administered with conventional mebendazole mixed with corn oil (Comparative example 2).

Figure 3B:
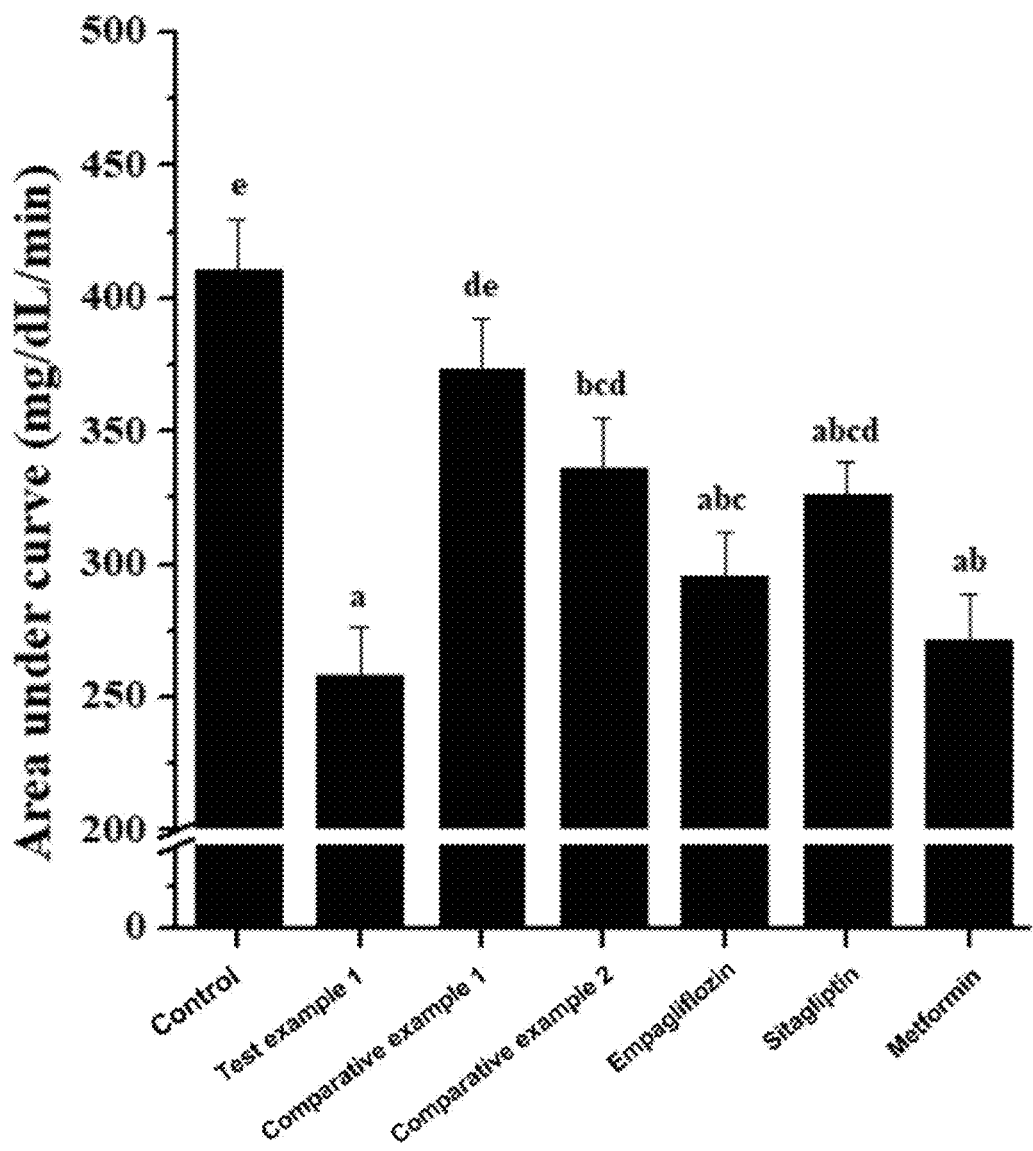
In FIG. 3B, the different letters a to e indicate that there is a statistically significant difference, i.e., $p<0.05$.

Furthermore, as a result of analyzing the area under curve of the oral sugar tolerance test, it was found that the test sample administration groups have more excellent effect of suppressing an increase in blood sugar level compared to Control as it is shown in FIG. 3B. In addition, compared to the group administered with conventional mebendazole mixed with water (Comparative example 1) and the group administered with conventional mebendazole mixed with corn oil (Comparative example 2), the group administered with the solubilized product of mebendazole (Test example 1), which has been processed by the solubilization method of the present invention, showed a significantly reduced area under curve, indicating that it has an excellent effect of suppressing an increase in blood sugar level.

2) Flubendazole

Figure 4:
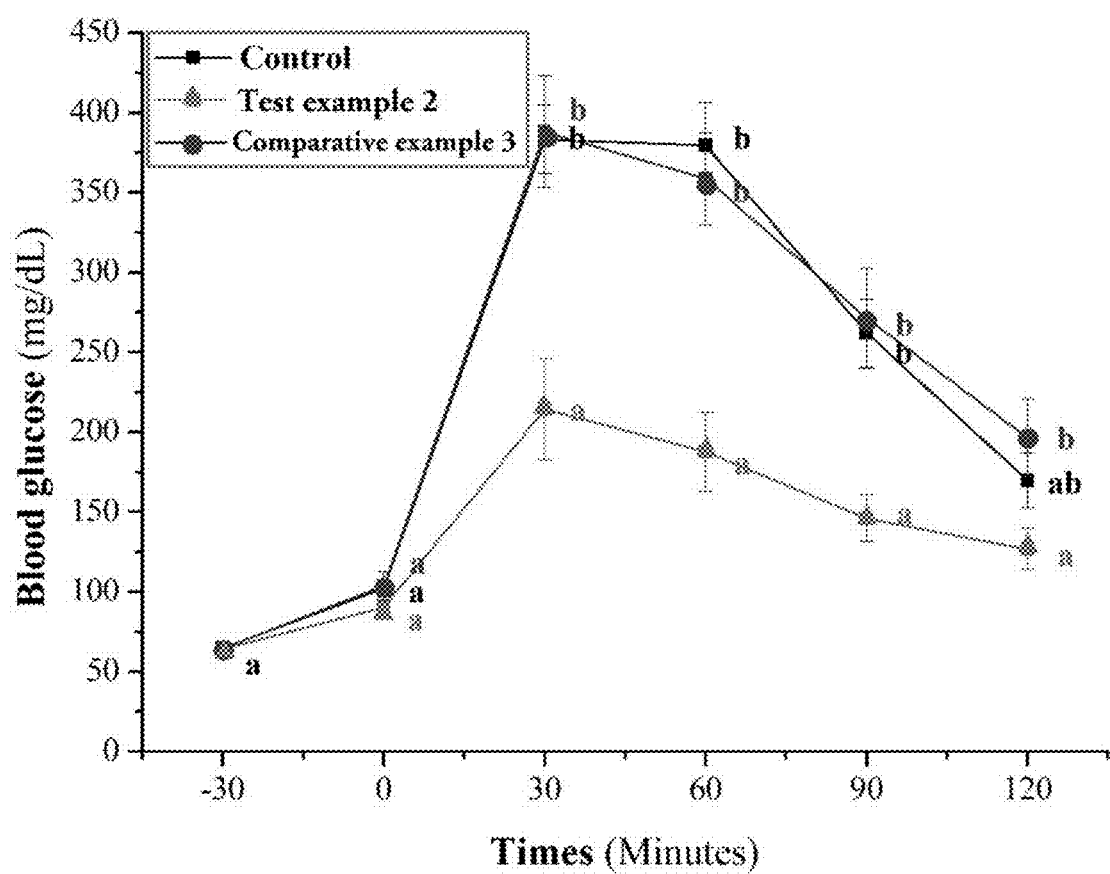
FIG. 4 shows the result of OGTT (oral glucose tolerance test) of flubendazole. Specifically, Control represents the group not treated with any test material, Test example 2 represents the group administered with the solubilized product of flubendazole which has been processed by the solubilization method of the present invention, and Comparative example 3 represents the group administered with conventional flubendazole mixed with water.

As a result of the oral glucose tolerance test (OGTT) using flubendazole, compared to Control, both the fasting glucose level and blood sugar level right after administering each test sample (i.e., 0 min) showed no significant difference in all test groups as it is illustrated in FIG. 4. However, 30 minutes after the administration of test sample, the group administered with solubilized product of flubendazole processed by the solubilization method of the present invention (Test example 2) showed a remarkably higher effect of suppressing an increase in blood sugar level compared to conventional flubendazole (Comparative example 3).

Figure 5:
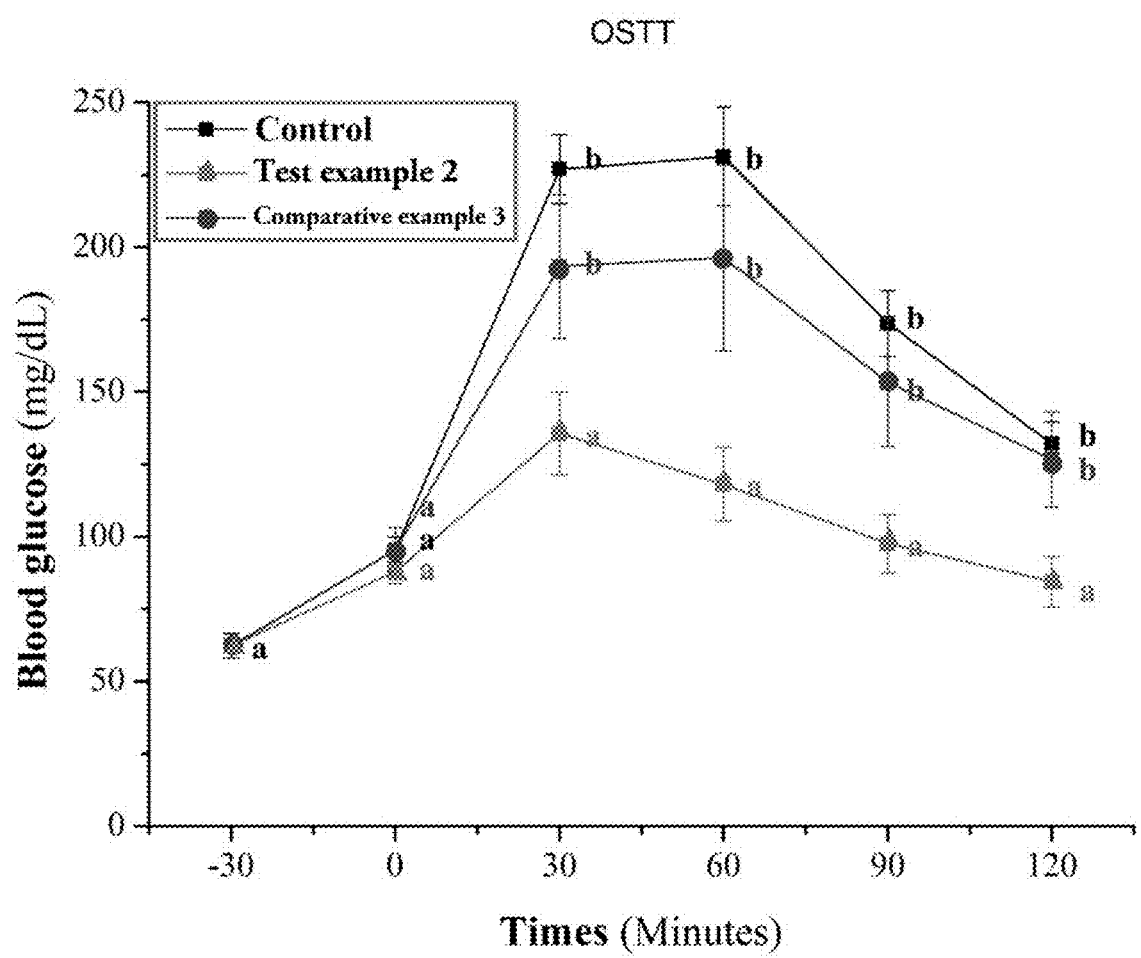
FIG. 5 shows the result of OSTT (oral sucrose tolerance test) of flubendazole. Specifically, Control represents the group not treated with any test material, Test example 2 represents the group administered with the solubilized product of flubendazole which has been processed by the solubilization method of the present invention, and Comparative example 3 represents the group administered with conventional flubendazole mixed with water.

Furthermore, as a result of the oral sugar tolerance test (OSTT) using flubendazole, compared to Control, both the fasting glucose level and blood sugar level right after administering each test sample (i.e., 0 min) showed no significant difference in all test groups as it is illustrated in FIG. 5. However, 30 minutes after the administration of test sample, the group administered with solubilized product of flubendazole processed by the solubilization method of the present invention (Test example 2) showed a remarkably higher effect of suppressing an increase in blood sugar level compared to conventional flubendazole (Comparative example 3).

3) Comparison of Anti-Diabetic Effect Among Various Solubilized Products of Benzimidazole-Based Compounds—Analysis of Area Under Curve Anti-diabetic effect was compared among various solubilized products of benzimidazole-based compound, specifically, solubilized product of mebendazole (Test example 1), solubilized product of flubendazole (Test example 2), and solubilized product of albendazole (Test example 3).

Figure 6:
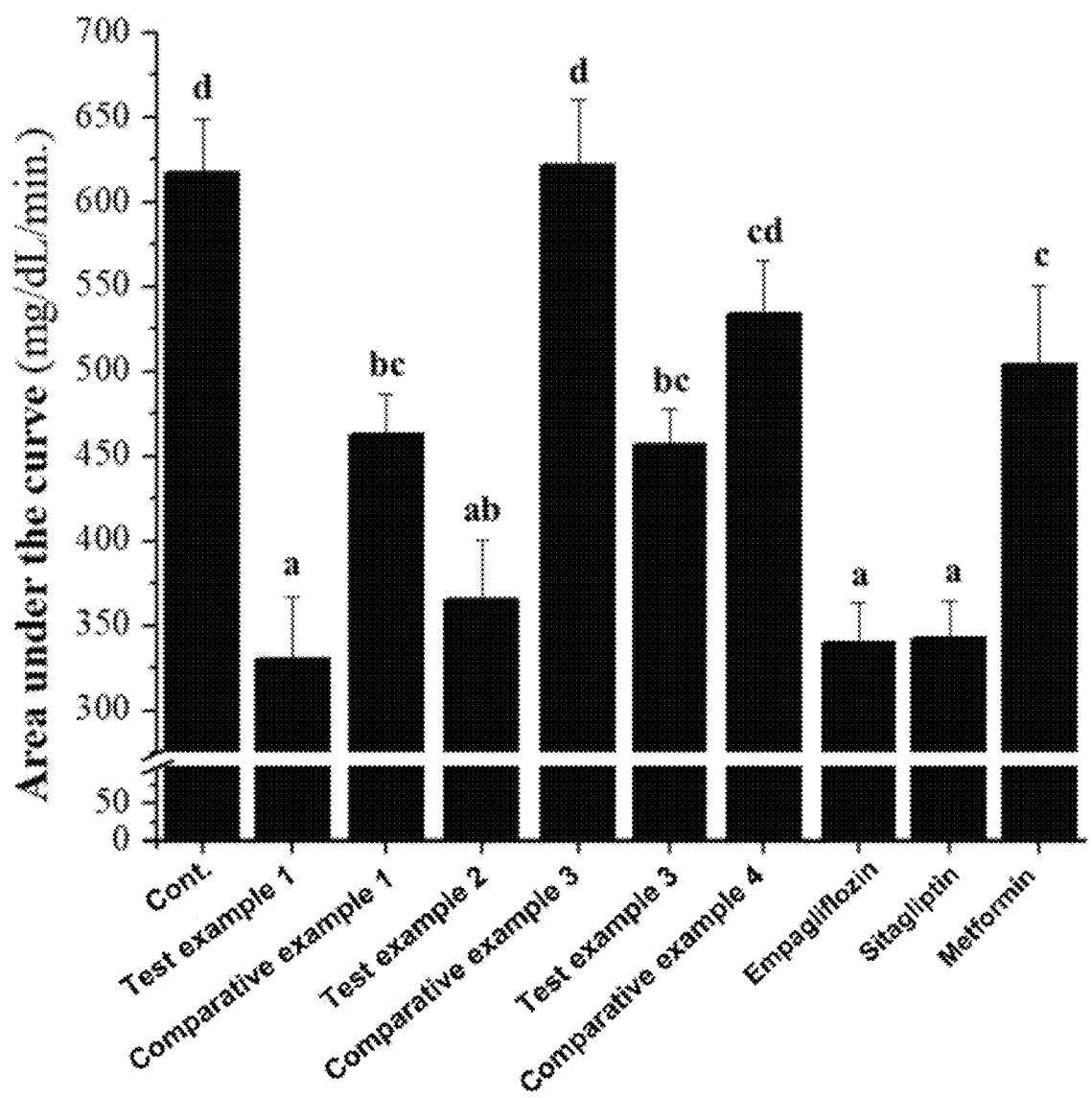
FIG. 6 shows the result of analyzing the area under curve obtained from OGTT of mebendazole, flubendazole, and albendazole, which are a benzimidazole-based compound. Specifically, Control represents the group not treated with any test material, Test example 1 represents the group administered with the solubilized product of mebendazole which has been processed by the solubilization method of the present invention, Test example 2 represents the group administered with the solubilized product of flubendazole which has been processed by the solubilization method of the present invention, Test example 3 represents the group administered with the solubilized product of albendazole which has been processed by the solubilization method of the present invention, Comparative example 1 represents the group administered with conventional mebendazole mixed with water, Comparative example 3 represents the group administered with conventional flubendazole mixed with water, and Comparative example 4 represents the group administered with conventional albendazole mixed with water. Empagliflozin, Sitagliptin, and Metformin correspond to a positive control to which empagliflozin, sitagliptin, or metformin has been administered as an oral therapeutic agent for treating diabetes.
Figure 7:
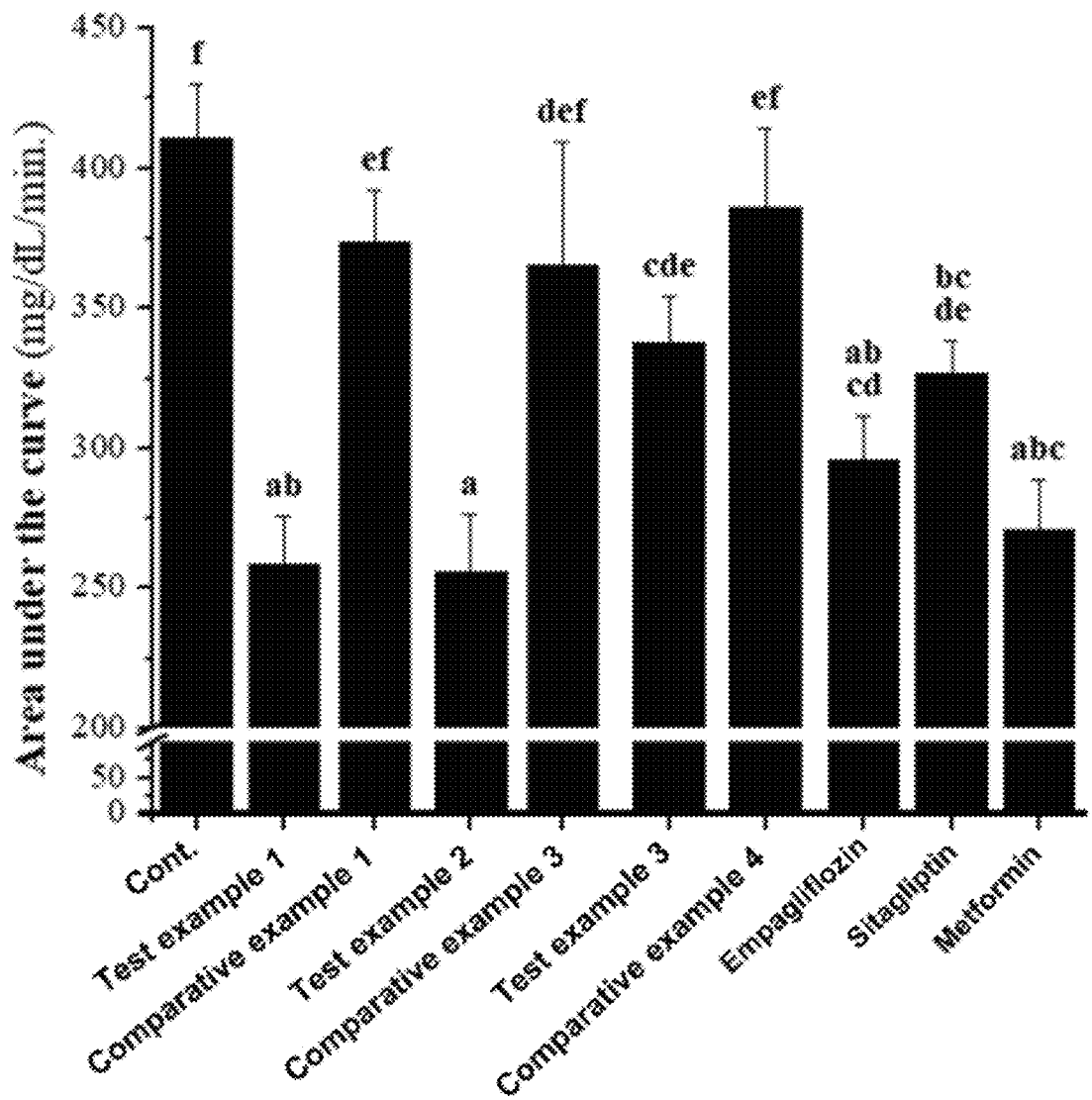
FIG. 7 shows the result of analyzing the area under curve obtained from OSTT of mebendazole, flubendazole, and albendazole, which are a benzimidazole-based compound. Specifically, Control represents the group not treated with any test material, Test example 1 represents the group administered with the solubilized product of mebendazole which has been processed by the solubilization method of the present invention, Test example 2 represents the group administered with the solubilized product of flubendazole which has been processed by the solubilization method of the present invention, Test example 3 represents the group administered with the solubilized product of albendazole which has been processed by the solubilization method of the present invention, Comparative example 1 represents the group administered with conventional mebendazole mixed with water, Comparative example 3 represents the group administered with conventional flubendazole mixed with water, and Comparative example 4 represents the group administered with conventional albendazole mixed with water. Empagliflozin, Sitagliptin, and Metformin correspond to a positive control to which empagliflozin, sitagliptin, or metformin has been administered as an oral therapeutic agent for treating diabetes.

As a result of analyzing the area under curve obtained from oral sugar tolerance test (OSTT) using benzimidazole-based compounds, it was found that the solubilized product of benzimidazole-based compound processed by the solubilization method of the present invention has more excellent effect of suppressing an increase in blood sugar level compared to conventional benzimidazole-based compound as illustrated in FIG. 6. In particular, after being processed by the solubilization method of the present invention, mebendazole and flubendazole exhibited more remarkable effect of suppressing an increase in blood sugar level compared to conventional mebendazole and flubendazole. This result is in a good match with the result of analyzing the area under curve obtained from oral sugar tolerance test (OSTT) of a benzimidazole-based compound, which is illustrated in FIG. 7.

What is claimed is:

1. A method for solubilizing a benzimidazole-based compound, the method comprising:
   preparing a first mixture solution by adding a benzimidazole-based compound to a solution in which water and glycerin are mixed with each other and subsequently homogenizing the first mixture;

admixing the first mixture solution with plant oil and an emulsifier in order to prepare a second mixture and subsequently homogenizing the second mixture; and after the admixing, allowing the second mixture to stand at 0 to 10° C. for 12 to 48 hours to obtain a solubilized product of the benzimidazole-based compound.

2. The method of claim 1, wherein the benzimidazole-based compound is at least one of mebendazole and flubendazole.

3. The method of claim 1, wherein the plant oil is canola oil.

4. The method of claim 1, wherein the emulsifier is sucrose fatty acid ester.

5. The method of claim 1, wherein the benzimidazole-based compound is mebendazole or flubendazole;

the homogenizing of the first mixture is performed at a speed of 3,000 to 5,000 rpm and a temperature of 50 to 80° C.;

the plant oil is canola oil;

the emulsifier is sucrose fatty acid ester;

the homogenizing of the second mixture is performed at a speed of 10,000 to 30,000 rpm and a temperature of 50 to 70° C.; and a condition of the allowing of the second mixture to stand is a temperature of 2 to 6° C. for 20 to 30 hours.

6. The method of claim 1, wherein the benzimidazole-based compound is 3 to 7 g of mebendazole or flubendazole;

the solution comprises a mixture of 100 g of water and 30 to 50 g of glycerin;

the homogenizing of the first mixture is performed at a speed of 3,500 to 4,500 rpm and a temperature of 65 to 75° C.;

the plant oil is 8 to 12 g of canola oil;

the emulsifier is 10 to 20 g of sucrose fatty acid ester; and the homogenizing of the second mixture is performed at a speed of 15,000 to 25,000 rpm and a temperature of 55 to 65° C.; and a condition of the allowing of the second mixture to stand is a temperature of 3 to 5° C. for 20 to 28 hours.

7. A solubilized product prepared by the method of claim 1.

8. A pharmaceutical composition comprising the solubilized product of claim 7 as an effective component.

9. A veterinary composition the solubilized product of claim 7 as an effective component.

10. A method for ameliorating or treating diabetes, the method comprising administering a composition comprising the solubilized product of claim 7 as an effective component to a subject in need thereof.

* * * * *